US011835521B2

(12) United States Patent
Ludwig et al.

(10) Patent No.: US 11,835,521 B2
(45) Date of Patent: Dec. 5, 2023

(54) METHOD FOR DETECTING ACUTE BORNA DISEASE VIRUS (BDV) INFECTIONS, AND DIAGNOSTIC KIT THEREFOR, IN PARTICULAR IN COMBINATION WITH METHODS FOR DISTINGUISHING ACUTE FROM CHRONIC AND LATENT BDV INFECTIONS, AND DIAGNOSTIC KITS THEREFOR

(71) Applicants: Hanns Ludwig, Berlin (DE); Liv Bode, Berlin (DE)

(72) Inventors: Hanns Ludwig, Berlin (DE); Liv Bode, Berlin (DE)

( * ) Notice: Subject to any disclaimer, the term of this patent is extended or adjusted under 35 U.S.C. 154(b) by 182 days.

(21) Appl. No.: 16/646,363

(22) PCT Filed: Sep. 11, 2018

(86) PCT No.: PCT/EP2018/074415
§ 371 (c)(1),
(2) Date: Apr. 29, 2020

(87) PCT Pub. No.: WO2019/052990
PCT Pub. Date: Mar. 21, 2019

(65) Prior Publication Data
US 2020/0271649 A1 Aug. 27, 2020

(30) Foreign Application Priority Data
Sep. 12, 2017 (DE) ..................... 10 2017 121 046.6

(51) Int. Cl.
*G01N 33/569* (2006.01)
*G01N 33/543* (2006.01)

(52) U.S. Cl.
CPC ... *G01N 33/56983* (2013.01); *G01N 33/5436* (2013.01)

(58) Field of Classification Search
None
See application file for complete search history.

(56) References Cited

FOREIGN PATENT DOCUMENTS

DE 197 58 017 C2 3/2000
DE 198 60 255 C2 3/2001

OTHER PUBLICATIONS

Bode et al., Molecular Psychiatry 2001, vol. 6, 481-489 (Year: 2001).*
Coutelier et al. (J Exp Med vol. 165 pp. 64-69 (Year: 1987).*
Jiang Y, et al., Front Neural Circuits. Dec. 8, 2021;15:769969 (Year: 2021).*
Bode et al., Clinical Micro Revs vol. 16, pp. 534-545 (Year: 2003).*
Bode et al.; "Borna disease virus-specific circulating immune complexes, antigenemia and free antibodies—the key marker triplet determining infection and prevailing in severe mood disorders"; Molecular Psychiatry, vol. 6, No. 4, Jul. 1, 2001, pp. 481-491.
Bode; "Human Bornavirus infection—towards a valid diagnostic system"; APMIS, vol. 116, No. 116, Jun. 1, 2008, pp. 21-39.
Bode et al.; "Borna disease virus infection, a human mental-health risk"; Clinical Microbiology Reviews, vol. 16, No. 3, Jul. 1, 2003, pp. 534-545.
Hsu et al.; "Borna disease virus p24 and p38/40 synthesized in a baculovirus expression system: virus protein interactions in insect and mammalian cells"; Virology, vol. 204, No. 2, Nov. 1, 1994, pp. 854-859.

* cited by examiner

*Primary Examiner* — Shanon A. Foley
*Assistant Examiner* — Myron G Hill
(74) *Attorney, Agent, or Firm* — WC&F IP

(57) ABSTRACT

One aspect of the present invention is directed to a method for detecting acute Borna Disease Virus (BDV) infections. According to the invention, the presence of heterodimers of p24 BDV phosphoprotein and p40 BDV nucleoprotein in a sample is determined by means of antibodies of both proteins using a sandwich ELISA. The invention also relates to a diagnostic kit for a sandwich ELISA for detecting mute BDV infections. Said kit uses a antibody of p24 BDV phosphoprotein and a second primary antibody of p40 BDV nucleoprotein, at least one reporter-molecule-labelled secondary antibody, means for immobilising a primary antibody on a surface, and instructions for carrying out the method according to the invention. The invention also relates to the combination of the method according to the invention and the new diagnostic kit with known methods for detecting circulating immune complexes (CIC) and antibodies. Acute BDV infections are thus distinguished from chronic and latent ones (humans and animals), allowing, for example, differential diagnosis and treatment monitoring for diseased individuals but also the identification of health risks depending on infection status in healthy carriers.

17 Claims, 4 Drawing Sheets

Specification includes a Sequence Listing.

| | E4265 | E3630 | E3727 | E3731 |
|---|---|---|---|---|
| New pAg 1:10 | 0.238 | 0.113 | 0.044 | 0.043 |
| Old pAg 1:10 | 0.055 | 0.068 | 0.045 | 0.058 |
| Old pAg 1:2 | 0.066 | 0.111 | 0.018 | 0.024 |

| | E3875 | E4064 | E3728 | E3667 | E3977 | E4173 | E4272 | E3731 | E3693 | E3838 | E3727 | E4265 | E3630 | E4113 | E4278 | E4123 |
|---|---|---|---|---|---|---|---|---|---|---|---|---|---|---|---|---|
| Ab | 0.055 | 0.027 | 0.033 | 0.067 | | | | 0.183 | 0.237 | | | 0.044 | 0.097 | | | |
| New pAg | | | | | 0.076 | 0.0815 | 0.0605 | 0.044 | 0.0755 | 0.142 | 0.029 | 0.2455 | 0.218 | 0.166 | 0.236 | 0.2195 |
| OC | 0.066 | 0.073 | 0.059 | 0.074 | 0.2835 | 0.2625 | 0.6325 | 0.607 | 0.587 | 0.8975 | 0.159 | 0.173 | 0.1305 | 0.306 | 0.715 | 0.366 |

mAb W1 binding sites on BDV N amino acid sequence and P binding domains mAb Kfu2 binding sites on BDV P amino acid sequence

METHOD FOR DETECTING ACUTE BORNA DISEASE VIRUS (BDV) INFECTIONS, AND DIAGNOSTIC KIT THEREFOR, IN PARTICULAR IN COMBINATION WITH METHODS FOR DISTINGUISHING ACUTE FROM CHRONIC AND LATENT BDV INFECTIONS, AND DIAGNOSTIC KITS THEREFOR

In a first aspect, the present invention is directed to a method for detecting acute Borna disease virus (BDV) infections. According to the invention, this involves determining the presence of heterodimers composed of p24 BDV phosphoprotein and p40 BDV nucleoprotein in a sample by means of sandwich ELISA. This determination encompasses the use of specific primary antibodies both against the p24 BDV phosphoprotein and against the p40 BDV nucleoprotein.

In a second aspect, a diagnostic kit for a sandwich ELISA for detecting acute BDV infections is provided. Said diagnostic kit comprises a first primary antibody and a second primary antibody, wherein one of these primary antibodies is directed against the p24 BDV phosphoprotein, whereas the other primary antibody is directed against the p40 BDV nucleoprotein, together with at least one secondary antibody labeled with a reporter molecule, means for immobilizing a primary antibody on a surface and instructions for carrying out the method according to the invention.

In a third aspect, the present invention is directed to distinguishing acute BDV infections from chronic and latent infections by, firstly, combining the method according to the invention and the diagnostic kit provided thereby with a method for detecting BDV infections in which the free-circulating immunocomplexes (CIC) composed of BDV antigens and specific antibodies attached thereto are detected by immunological assays, as described in DE 19758017 C2 for example, and by, secondly, additionally using a method for detecting BDV infections in which free-circulating BDV antibodies in the infected host are detected by immunological assays. Accordingly, diagnostic kits according to the invention comprise means for detecting BDV CIC and an appropriate diagnostic kit for detecting BDV antibodies.

Lastly, the use of the method according to the invention for the diagnosis of acute BDV infections and/or the course monitoring thereof is provided. Especially in combination with the methods for detecting BDV CIC and BDV antibodies, the method according to the invention is provided for the differentiation of acute BDV infections from chronic and latent infections and/or the course monitoring thereof and the exclusion of a BDV infection. It is equally suitable for humans and animals. The state in which the infection is and the course of said infection has direct effects on the possibility of an antiviral therapy in clinically ill individuals.

PRIOR ART

The Borna disease virus (BDV) is taxonomically the lead virus of the species "Mammalian 1 bornavirus" in the virus family "Bornaviridae", which belongs to the "Mononegavirales" order. Its virus strains, which are genetically identical to an extent of more than 95%, infect brain and blood cells in humans and many mammals and are widespread worldwide. In the case of horses, it is the pathogen of Borna disease. Borna viruses are enveloped viruses (90 nm diameter) containing a negative-sense nonsegmented single-stranded (NSS) RNA of 8910 kilobases that encodes six genes. Borna viruses multiply in the nucleus of the host cell and are among the evolutionarily oldest viruses, which have coexisted with primate ancestors for at least 40 million years and have even left permanent traces in terms of their genetic material as far as humans. Today, BDV infections occur in many farm and domestic animals (including horse, sheep, cattle, cat) and humans. They remain in the infected organism for life (persistent infection without cell destruction), preferentially affect the part of the brain that is old in terms of evolution (limbic system) and are involved in behavioral and mood changes.

It is assumed that every third person of adult age in Germany is infected with Borna viruses unnoticed, i.e., without clinical symptoms (Bode and Ludwig, 2003). In the case of every sixth infected individual (16-17%), there is an increased risk of suffering from a mental disorder in the course of life. Based on the entire population, every twentieth person (5 out of 100 people; 5%) has an increased risk of disease. What is suspected to be the most important risk factor is chronic stress, which weakens the immune system in the long term and favors the activation of latent Borna viruses.

The Borna virus preferentially affects the nerve cells of the limbic system of the brain. These central brain regions control behavior and emotions and are involved in learning processes and memory formation. The virus multiplies primarily in nerve cells and can, via the processes thereof, spread throughout the nervous system. This involves the formation of the virus proteins N (p40 nucleoprotein) and P (p24 phosphoprotein) (antigens) in excess. In the brain of symptomatic patients (e.g., in the case of depression), they contribute to dysfunctions in the equilibrium of brain messenger substances (evidence from animal experiments).

In animals, BDV infections are associated with episodic behavioral disorders, including apathy, attention loss and movement coordination disorders. In humans, acute or chronic Borna virus infections have been found much more frequently in acute depressive episodes, in compulsive disorders and in chronic fatigue syndrome, for example, than in healthy persons. Therefore, it has been suspected for years that Borna viruses are involved in the very complex disease process, but this is still considered controversial (Bode and Ludwig, 2003). An involvement is indicated by the proven use of an antiviral therapy with amantadine. Endogenous recurrent depressions, unipolar or bipolar, are, with at least 5% lifetime prevalence, among the major psychiatric disorders in Germany and worldwide.

There is therefore a need for reliable diagnostic systems for capturing BDV infections, both in the monitoring of infection phases in sick individuals and for course and therapy monitoring, and for capturing undetectedly infected asymptomatic carriers, on a population basis for epidemiological reasons or on a personal basis for ascertaining the individual risk of disease.

For the assessment of the infection phases (acute, chronic, latent), the increased expression of BDV antigens (N and P) in the blood has been found to be the critical activity parameter. It correlates well with clinical disease (humans and animals), is quantitatively measurable and important for estimating the clinical course. The determination of antigen also cannot be replaced with the detection of the viral nucleic acid in the PBMCs via amplification using nested RT-PCR or real-time RT-PCR, since this can determine only the virus itself, but not the activity thereof. Nowadays, the diagnosis of Borna virus infections is nevertheless carried out in many places with detection of the viral genome or is limited serologically to the detection of antibodies by means of various serological methods. However, a negative detection of specific antibodies alone is not a suitable instrument for excluding a BDV infection, since free antibodies are, during an antigen-releasing multiplication phase, bound in the form of circulating immunocomplexes (CIC) in the serum of the infected individual and can temporarily drop below the detection limit.

In recent years, diagnostic methods based on ELISA techniques have been carried out, in which BDV-specific immunocomplexes (CICs) and also viral proteins and possibly free-circulating antibodies are measured (Bode et al., 2001). Specific monoclonal antibodies are used in this case. The amino acid sequences of the BDV nucleoprotein p40 and of the phosphoprotein p24 have been known since the first two complete genomes of two BDV virus strains were sequenced in 1994 (Briese et al., 1994; Cubitt et al., 1994). In the case of the nucleoprotein, it was possible to create a ribbon model of the three-dimensional structure (Rudolph et al., 2003).

The key reagents for the BDV ELISA assays, the monoclonal antibodies W1 (anti-N) and Kfu2 (anti-P), were characterized in terms of their basic properties (Ludwig et al., 1993). The BDV CICs are the most frequently detectable infection markers and have hitherto been found to be optimal for corresponding diagnostic assays.

On the basis thereof, DE 19758017 C2 relates to corresponding methods for detecting BDV infections, in which the free-circulating immunocomplexes composed of BDV antigens and specific antibodies attached thereto are detected by immunological assays. This property right furthermore relates to a corresponding diagnostic kit, as mentioned at the start. An extension thereof is found in DE 19860255 C2, directed to a method for detecting BDV infections, wherein the antigen detection is carried out in a plasma sample, cerebrospinal fluid or urine.

Corresponding blood assays for BDV CIC are used. The use of the immunocomplex (CIC), which is only detectable when the viruses have multiplied in phases, is highly suitable for indicating chronic infections in the positive case. The additional earlier antigen assay indicated a bout in the positive case. A negative CIC assay required the additional antibody ELISA in order to detect a latent infection or to exclude the infection.

Current diagnostic systems and methods are based on the detection of CIC, wherein, on the basis of a sandwich ELISA, the antigen part in the CIC is bound using monoclonal antibodies from a first species and then the antibody part of the bound CIC is detected using an enzyme-labeled secondary anti-antibody from another species and a substrate reaction (color change) which corresponds to the relative amount of the CIC in the sample.

The CIC ELISA has proven effective as a basic assay for detecting a chronic BDV infection. For acute BDV infection detection, which is particularly important for clinically ill individuals, this assay alone is not suitable. The antigen assay up to now is constrained by a high sample volume and limited resources and thus not usable as a diagnostic kit in the long run.

The present invention closes this gap by providing a completely new assay method for acute BDV infections. Owing to combination with CIC assay and antibody assay, the new method is capable of distinguishing between acute, chronic and latent infections and of thereby raising BDV diagnostics to a hitherto unreached level of informative value with a high standard of quality.

The present invention provides a completely new assay method for acute BDV infections. It has now been possible to identify the specific binding profiles of the monoclonal antibodies "W1" and "Kfu2" that were used in the methods according to DE 19758017 C2, which both recognize potent conformational epitopes on, respectively, the BDV N protein and P protein (Bode, 2008). The present invention focuses on the recognition of the active, phosphorylated form of the P protein and, in particular, of heterodimers N/P. The monoclonal antibodies described here are therefore particularly highly suitable for the new assay method and the assay methods combined therewith.

DESCRIPTION OF THE INVENTION

It is an object of the present invention to provide a method for detecting acute BDV infections and corresponding diagnostic kits based on ELISA, especially sandwich ELISA, techniques. It is a further object to provide improved methods for differential diagnosis.

In a first aspect, the invention is directed to a method for detecting acute Borna disease virus (BDV) infections, comprising the step of determining the presence of heterodimers composed of p24 BDV phosphoprotein (Seq. ID No. 2) and p40 BDV nucleoprotein (Seq. ID No. 1) in a sample by means of a sandwich ELISA, a first primary antibody being present in an immobilized state and a second primary antibody being added in a nonimmobilized state after incubation of the sample with the immobilized first antibody, characterized in that the first primary antibody is directed against the p24 BDV phosphoprotein and the second primary antibody is directed against the p40 BDV nucleoprotein or vice versa.

It became apparent that the detection of an acute, currently active infection is possible, especially in an embodiment wherein the first primary antibody only recognizes phosphorylated P protein (Bode, 2008). The phosphorylated form is essentially only detectable in the active state of the infection.

In a second aspect, the present invention is directed to a diagnostic kit for a sandwich ELISA for detecting acute BDV infections. Said diagnostic kit comprises a first primary antibody and a second primary antibody, one of said primary antibodies being directed against the p24 BDV phosphoprotein and the other primary antibody being directed against the p40 BDV nucleoprotein, the primary antibody against the p24 BDV phosphoprotein preferably being present in an immobilized state. The kit furthermore comprises at least one secondary antibody labeled with a reporter molecule, optionally means for immobilizing the primary antibody on a surface, especially means for immobilizing the primary antibody against the p24 BDV phosphoprotein, and instructions for carrying out the method according to the invention.

In a third aspect, the present invention is directed to distinguishing acute BDV infections from chronic and latent infections. To distinguish chronic infections, the present invention is furthermore combined with methods, as described in DE 19758017 C2 for example, for detecting BDV infections in which the free-circulating immunocomplexes (CIC) composed of BDV antigens and specific antibodies attached thereto are detected by immunological assays.

To distinguish latent infections, the method according to the invention is combined with methods for detecting BDV infections in which free-circulating BDV antibodies against the p24 protein and/or the p40 protein in the infected host are detected by immunological assays.

DETAILED DESCRIPTION OF THE INVENTION

The present invention relates to a method for detecting acute Borna disease virus (BDV) infections, comprising the step of determining the presence of heterodimers composed of p24 BDV phosphoprotein and p40 BDV nucleoprotein in a sample by means of a sandwich ELISA, a first primary antibody being present in an immobilized state and a second primary antibody being added in a nonimmobilized state after incubation of the sample with the immobilized first antibody, characterized in that the first primary antibody is directed against the p24 BDV phosphoprotein and the second primary antibody is directed against the p40 BDV nucleoprotein or vice versa. It became apparent that, by using the two stated primary antibodies, that is, firstly, the antibody against the p24 BDV phosphoprotein and, secondly, the primary antibody against the p40 BDV nucleoprotein, it is possible to detect heterodimers formed from said two proteins. Such heterodimers and, in particular, heterodimers in which the p24 is present in phosphorylated form are present especially in the acute phase. As a result, it is possible to unequivocally detect an acute BDV infection.

The CIC ELISA has proven effective as a basic assay for detecting a chronic BDV infection. For acute BDV infection detection, which is particularly important for clinically ill individuals, this assay alone is not suitable. The antigen assay up to now is constrained by a high sample volume and limited resources and thus not usable as a diagnostic kit in the long run.

The present invention closes this gap by providing a completely new assay method for acute BDV infections. Owing to combination with CIC assay and antibody assay, the new method is capable of distinguishing between acute, chronic and latent infections and of thereby raising BDV diagnostics to a hitherto unreached level of informative value with a high standard of quality.

The present invention provides a completely new assay method for acute BDV infections because, inter alia, it was possible to decipher the binding profiles of the monoclonal antibodies "W1" and "Kfu2" that were used in the DE 19758017 C2 methods, which monoclonal antibodies define especially the high specificity of the new method. The amino acid sequences of the binding sites which form the respective conformational epitopes are named for the first time here (Seq. ID. Nos. 3 to 7 for the p40 and Seq. ID. Nos. 8 to 10 for p24). They are essential molecular constituents of the properties of the abovementioned monoclonal antibodies.

The specificity requirements of the primary antibodies are such that they are preferably monoclonal and recognize conformational epitopes which do not overlap with the BDV phosphoprotein binding domain on the BDV nucleoprotein so that heterodimers can be recognized. Furthermore, the requirements of the antibodies directed against the phosphoprotein are preferably such that the epitope includes the main phosphorylation site (Schwemmle et al., 1997) and only the active phosphorylated form of the protein recognized.

Therefore, in one embodiment, the first primary antibody is directed against the phosphorylated p24 BDV phosphoprotein. In said embodiment, what are detected according to the invention are only p24 phosphorylated heterodimers composed of p24 BDV phosphoprotein and p40 BDV nucleoprotein.

The BDV antigens p24 and p40 are formed to an increased extent in a bout of activity and discharged into the blood plasma in the body. These p24 and p40 proteins then form in the blood preferably heterodimers composed of p24 and p40, the p24 protein in the heterodimer being present in a phosphorylated state after active viral multiplication and secretion into the plasma. The phosphorylation is an active process in the host cell after formation of the viral P protein.

The detection of an acute, currently active BDV infection is especially possible because heterodimers and, here in particular, heterodimers containing phosphorylated BDV p24 phosphoprotein are detected using the method according to the invention. In one embodiment, said antibody directed against the phosphorylated form is a monoclonal antibody, for example a monoclonal antibody of mouse origin. In one embodiment, said antibody is the first primary antibody which has been immobilized on a surface.

The detection of an acute, currently active BDV infection is ensured because the phosphorylated form-binding monoclonal antibody, such as the primarily used mAb "Kfu2", see Ludwig et al., 1993, recognizes a conformational epitope formed from three binding sites on the active phosphorylated BDV P protein (Seq. ID Nos. 8, 9 and 10). The second primary monoclonal antibody, such as the primarily used mAb "W1", see Ludwig et al., 1993, recognizes a conformational epitope formed from five binding sites on the BDV N protein (Seq. ID Nos. 3, 4, 5, 6 and 7). There is no overlap of these binding sites on both proteins with the P protein binding domain (Berg et al., 1998) on the N protein. As a result, it is possible to recognize N/P heterodimers (Bode, 2008).

The immobilization of the first primary antibody on the surface is effected directly in one embodiment and, in an alternative embodiment, the immobilization is effected via a first secondary antibody which, for example, binds the primary antibody in a species-specific manner, especially in a subclass-specific manner, without the activity of said primary antibody in relation to binding to the heterodimer composed of p24 BDV phosphoprotein and p40 BDV nucleoprotein, especially the p24 phosphorylated BDV phosphoprotein, being impaired.

The immobilization of the primary antibody or the first secondary antibody on a surface is effected according to customary methods. A person skilled in the art is aware of appropriate methods. The immobilization is customarily effected via the Fc region of the secondary antibody or the primary antibody.

The presently described method for detecting infection in the serum/plasma is primarily based on the infection of peripheral blood mononuclear cells (PBMCs) in such a way that the virus multiplication proceeding in bouts leads to the secretion of N and P protein (antigens) from PBMCs (and sources in the body that are still unknown) into the blood plasma (acute infection), antibodies are formed later on in the host and said antibodies are bound to the antigens to form circulating immunocomplexes (CIC), which indicate a chronic infection.

The term "detection" is presently used to mean that both a first qualitative detection and a quantitative determination of the concentration of heterodimers is possible.

In a further embodiment of the method according to the invention, the nonimmobilized primary second antibody is determined via a second secondary antibody comprising a reporter molecule.

The expression "reporter molecule" is presently understood to mean a molecule which, firstly, allows a direct measurement, for example also known as a label or tag. Secondly, said reporter molecule can have a first binding parameter, which is accordingly detected with a further labeled molecule (second binding partner) as a binding pair. Lastly, the reporter molecule can comprise a catalyst, such as an enzyme.

Examples of suitable reporter molecules encompass known reporter molecules, such as dyes, including fluorescent dyes, radioactive molecules. Alternatively, said reporter molecule can be a known binding pair, such as a biotin-streptavidin or biotinavidin pair. Lastly, the reporter molecule can be a catalyst, especially an enzyme. Known enzymes include alkaline phosphatase, peroxidase, especially horseradish peroxidase, and other, customary enzymes.

A person skilled in the art is aware of appropriate reporter molecules, as used especially in immunobased detection methods, especially in ELISA methods.

In one embodiment, the second secondary antibody is one comprising biotin as reporter molecule. Said antibody is then detected with the aid of an appropriate binding partner, such as avidin or streptavidin coupled with an enzyme, such as alkaline phosphatase (AP) or horseradish peroxidase (HRP).

Alternatively, said second secondary antibody can be directly labeled with an enzyme, such as AP or HRP.

In one embodiment, the two secondary antibodies are from the same species and, in another embodiment, the two secondary antibodies originate from different species. In one embodiment, the two secondary antibodies are those which, originating from the same species or different species, recognize different immunoglobulin subclasses of the species of the primary antibodies.

In one embodiment of the present invention, the primary antibodies can be those wherein the first primary antibody and the second primary antibody originate from different species and/or wherein said primary antibodies are monoclonal antibodies. In one embodiment thereof, the primary antibodies originate from the same species, but from different immunoglobulin classes or different immunoglobulin subclasses. In one embodiment, the primary antibodies originate from mouse and are monoclonal antibodies, for example wherein one of the primary antibodies is one of the subclass IgG1 and the second primary antibody is an antibody from mouse of the subclass IgG2.

If the primary antibodies originate from different subclasses, such as IgG1 and IgG2, then the secondary antibodies are preferably those which specifically detect said subclasses, i.e., bind to said subclasses. Thus, cross-reactivity can be minimized.

The primary antibodies can optionally be modified such that they comprise other components or are single-chain antibodies. The primary antibodies are distinguished in that they specifically recognize the corresponding protein of the BDV and comprise the necessary binding site, if required, for the secondary antibody. If the primary antibody is directly coupled to the surface, said binding site for the secondary antibody need not be present. In the case of direct coupling, the primary antibody can be modified such that binding to the surface is favored.

A person skilled in the art is aware of suitable measures for modifying the primary antibodies by appropriate molecular biology methods. In this process, the specificity of the primary and optionally secondary antibody is maintained, while components which possibly cause cross-reactivity are taken out. These modifications support the improvement in specificity.

The expression "antibody", as used herein, encompasses monoclonal antibodies, polyclonal antibodies and chimeric antibodies, unless otherwise stated. The antibodies can be produced from recombinant sources and/or by hybridoma cells. Alternatively, transgenic animals, etc., can be used. The antibodies can also be present as antibody fragments if they retain the specificity for the p24 BDV phosphoprotein and p40 BDV nucleoprotein. The expression "antibody fragment", as used herein, encompasses suitable scFv, dsFv, ds-scFv, dimers, minibodies, diabodies, but also fab, fab- or f(ab')2 fragments.

Such fragments can be produced by appropriate recombinant techniques.

In the present invention, preference is given to monoclonal antibodies which are produced using suitable conventional techniques, i.e., hybridoma techniques. Using this technique in combination with infection and immunization of mice, it was possible to select antibodies which each recognize epitopes on the native conformation of the proteins N and P. Conformational epitopes, as present for "W1" and "Kfu2", have particularly high binding constants for native BDV proteins (Bode, 2008), which are not achieved for linear epitopes by monoclonal antibodies produced with the aid of recombinant proteins.

The reporter molecule, also referred to as marker or label, allows the direct or indirect generation of detectable signals. Suitable labels or markers are radioisotopes, as are generally known, but especially also dyes, such as fluorescent dyes (fluorophores), or chemiluminescence compounds (chromophores); examples thereof are fluorescein isothiocyanate (FITC), rhodamine or luciferin. In one embodiment, the reporter molecules are enzymes, especially alkaline phosphatase or β-galactosidase or horseradish peroxidase, which convert substrates with color change as the signal. Imaging means such as magnetic or paramagnetic marker molecules or metal ions are likewise encompassed. In one embodiment, the reporter molecule is coupled to the secondary antibody via a binding partner of a binding pair such as, for example, the streptavidinbiotin binding pair or biotinavidin binding pair. A person skilled in the art is aware of suitable binding pairs.

In a further third embodiment, what is furthermore detected besides the detection of the heterodimer is additionally a detection of circulating immunocomplexes (CIC) composed of BDV antigens and specific antibodies attached thereto. The CIC BDV antigens may include all or a portion of p24 protein and/or p40 protein. Appropriate detection methods are, for example, known from DE 19758017 C2. The combination of the detection of the heterodimer in accordance with the present invention, especially the phosphorylated heterodimer, with the detection of circulating immunocomplexes (CIC) and specific antibodies bound therein from the individual increase the specificity of detecting a BDV infection, especially also the differentiation between acute BDV infection and chronic BDV infection. In a further embodiment, what is carried out besides the detection of the heterodimer and the CIC is the detection method for BDV antibodies that is also known from DE 19758017 C2. The combination of the detection of the heterodimer in accordance with the present invention with the detection of CIC and the detection of free antibodies allows the differentiation between acute, chronic and latent infection in the individual; see also FIG. 1.

The method according to the invention is especially one which allows diagnosis and/or course monitoring and/or is used for exclusion of a BDV infection, for example in the case of psychiatric and/or neurological disorders. This means that the method is, according to the invention, one which diagnoses an acute BDV infection. In another aspect, it is a method which is suitable for course monitoring in combination with CIC assay and antibody assay and especially for differentiation between acute, chronic and latent BDV infection. It is likewise suitable, in the above combination, for excluding BDV infections of various activity states in the case of psychiatric and/or neurological disorders.

In a further aspect, the present invention is directed to a diagnostic kit for a sandwich ELISA for detecting acute BDV infections. Said diagnostic kit comprises a first primary antibody and a second primary antibody. One of these two primary antibodies is directed against the p24 BDV phosphoprotein, and the other primary antibody is directed against the p40 BDV nucleoprotein. The diagnostic kit furthermore comprises suitable secondary antibodies, but at least one secondary antibody labeled with a reporter molecule. Optionally, what are furthermore provided are means for immobilizing a primary antibody on a surface and instructions for carrying out the method according to the invention using said kit.

In one embodiment, the primary antibodies and secondary antibodies that are present in the kit are those as presently described. The primary antibodies are especially those where one of said primary antibodies recognizes the phosphorylated protein of the p24 phosphorylated heterodimer, whereas the second primary antibody recognizes the p40 BDV nucleoprotein in the heterodimer. The secondary antibodies are those secondary antibodies as defined in the present application, especially those which originate from the same species and/or those which recognize different subclasses of primary antibodies.

In one embodiment, the diagnostic kit furthermore comprises means for detecting CIC formed from BDV antigens and specific antibodies attached thereto from the individual. Said means are especially appropriate monoclonal antibodies.

Lastly, the use of the method according to the invention and the diagnostic kit for diagnosis and/or course monitoring and/or for exclusion of BDV infections in the case of psychiatric and/or neurological disorders is provided.

The method according to the invention and the diagnostic kits according to the invention and the use of the method and the diagnostic kit make it possible to set up a treatment plan for the BDV infection in the examined individual as an option for the treating physician. Accordingly, a method for treating acute BDV infections is provided, comprising the method for detecting an acute BDV infection in accordance with the present invention and, in the case of diagnosis of an acute BDV infection, treating same with the antiviral medicament amantadine sulfate (AS). Said medicament has proven to be highly potent against natural Borna viruses. AS is a medicament which has been authorized for the antiviral therapy of virus influenza (influenza A) for over 40 years and which can be prescribed for treatment of Borna virus infection (off-label use). AS inhibits the multiplication of natural Borna viruses and thus the formation of the harmful viral proteins (antigens) (Bode and Ludwig, 2003). The majority of infected patients with acute and/or chronic depression (70%) benefit lastingly through improvement in the symptoms (Dietrich et al., 2000; Ferszt et al., 1999) in parallel to the decline in the virus markers in the blood. It was also possible to demonstrate the antiviral effect of AS in infected patients whose depression was already in remission (no more symptoms of depression). Course monitoring in the blood plasma using the ELISA assay for determining the CIC, the antigen (pAG, earlier assay) and the antibodies according to method DE 198 60 255 C2 showed a significant reduction in these assay parameters after 14 weeks (Dietrich and Bode, 2008).

AS is demonstrably effective in vitro in a dose-dependent manner in the case of natural Borna viruses of humans and horses. The titer of the human virus isolate Hu-H1 from a depressive bipolar patient (Bode et al., 1996) in human oligodendroglial cells is no longer detectable within 10 to 33 days depending on amantadine sulfate concentrations of 1.2 μg/ml to 0.4 μg/ml. The concentration of 0.4 μg/ml AS correlates with the concentration achieved in the patient plasma in the case of oral ingestion of 200 mg of AS per day (Bode et al., 1997).

Furthermore, a method for treating psychiatric and/or neurological disorders is provided, comprising the detection of a BDV infection, especially an acute BDV infection, in accordance with the present invention and in the case of detection of a BDV infection, especially detection of an acute BDV infection or detection of a chronic activated infection in combination with CIC. A treatment option for the individual can be a treatment with 2-4 mg of AS per kg of body weight per day orally. In the case of a patient weighing 75 kg, this is 150 to not more than 300 mg of AS per day. Gradually increase the dose at the start, with 1 mg of AS per kg of body weight for the first three to four days. Dose regimen: in the morning in the gradual dose-increase phase. Dose regimen thereafter: starting with 2 mg of AS per kg of body weight, with half of the daily dose in the morning and the other half of the daily dose at noon (1-1-0). In the event of unrest in the first one to two weeks or problems with falling asleep, take the daily dose only in the morning (1-0-0).

Furthermore, a method for treating a BDV infection is provided, wherein the treatment is monitored as part of a course monitoring with the aid of the method according to the invention. In this connection, the treatment is effected such that the treatment can be ended after three months in the event of a positive course of the treatment that is characterized by a clinical improvement after the first four to six weeks on average and by a reduced virus activity characterized by a reduction in the heterodimers and/or the CIC in the blood plasma. Monitoring of the blood values for antigen (heterodimers) and CIC is obligatory after three months. Before stopping the medicament, there should be no more detectable heterodimers, and lower CIC values in comparison with the state before the treatment. The medicament should be gradually withdrawn with dose reduction over four to seven days.

In the case of a delayed course of the treatment, characterized by slight clinical improvement after the first four to six weeks and only a slight change in or unaltered detection of these heterodimers, especially the phosphorylated heterodimers, optionally in combination with CIC, the treatment should be continued for the duration of three months and the therapy should possibly be altered. As a precaution, in the event of a slight clinical improvement, course monitoring after 6 weeks with the aid of the method according to the invention in combination with CIC is obligatory and an adjustment of the therapeutic dose is advisable in the event of little or unchanged antigen and/or CIC values. If the dose was previously 2 mg of AS per kg of body weight, an increase to 3 mg of AS per kg of body weight to at most 4 mg of AS per kg of body weight is advisable in the described constellation.

Customary therapies for a BDV infection in depressive psychiatric patients include the prescription of established antidepressants, such as, for example, of tricyclic antidepressants or of serotonin reuptake inhibitors (SSRIs). AS is excreted unaltered in the kidneys, and there are no degradation products in the liver and, as a result, negligible undesired interactions, or none, with these medicaments. Therefore, without stopping the above therapeutics, AS can be additionally prescribed to control the BDV infection. In the case of patients with renal failure who require dialysis, an undesired increase in the blood levels of AS can occur. Therefore, in the case of such patients, the ingestion of the abovementioned dose is only recommended every second or third day, and optionally weekly monitoring of the blood levels of the medicament.

The sample used can be body fluid and body tissue in isolated form. Especially suitable samples originate from the blood, for example in the form of serum or plasma. Further suitable samples are cerebrospinal fluid in the case of neurological patients, but they do not exclude an infection in the case of a negative finding, and so a sample from blood, as serum or plasma, is obligatory. In one embodiment, the sample is an isolated sample from blood plasma or blood serum.

The invention will be further elucidated with the aid of examples without being restricted thereto.

EXAMPLES

Isolated blood samples from individuals showing a BDV infection are provided, the status of the infection being acute, chronic or latent or no infection being present.

Table of medical personnel from Chongqing study

| Code Sample | Medical personnel (MP) | Sex | Age | Antigen heterodimers Diluted 1:10 | CIC Diluted 1:20 | Antibody Diluted 1:100 | Infection status |
|---|---|---|---|---|---|---|---|
| E3875 | No details | female | 50 | | 0.066 | 0.055 | none |
| E4064 | Administration | male | 51 | | 0.073 | 0.027 | none |
| E3728 | Ophthalmology | female | 29 | | 0.059 | 0.033 | none |
| E3667 | Gastroenterology | male | 28 | | 0.074 | 0.067 | none |
| E3977 | Infection department | female | 48 | 0.076 | 0.2835 | | chronic |
| E4173 | Breast surgery | female | 47 | 0.0815 | 0.2625 | | chronic |
| E4272 | Surgical preparation | female | 49 | 0.0605 | 0.6325 | | chronic |
| E3731 | Ophthalmology | female | 52 | 0.044 | 0.607 | 0.183 | chronic |
| E3693 | Heart surgery | female | 59 | 0.0755 | 0.587 | 0.237 | chronic |
| E3838 | No details | female | 26 | 0.142 | 0.8975 | | acute |
| E3727 | Ophthalmology | female | 55 | 0.029 | 0.155 | | chronic |
| E4265 | Experimental research | female | 41 | 0.2455 | 0.173 | 0.044 | acute |
| E3630 | Retired | female | 35 | 0.214 | 0.1305 | 0.097 | acute |
| E4113 | Rehabilitation | male | 81 | 0.166 | 0.306 | | acute |
| E4278 | Surgical preparation | male | 29 | 0.236 | 0.715 | | acute |
| E4123 | Rehabilitation | male | 30 | 0.2195 | 0.366 | | acute |
| E3968 | Positive control MP | male | 57 | 1.9835 | 0.3675 | 0.3025 | acute |
| Student | Negative control | | | | 0.0495 | 0.068 | none |

Assessment of the assay results (standard for all BDV EIA assays)
Cut-off = 0.100.
Negative <= 0.1;
borderline > 0.1-0.12;
(+) weakly positive > 0.12-0.15;
1+ positive > 0.15-0.3
2+ positive > 0.3-0.6;
3+ positive > 0.6-1.0;
4+ positive > 1.0.

The samples come from a large study which had been carried out in a university hospital in Chongqing, China, using the CIC assay and additionally the antibody assay and a real-time RT-PCR (Liu et al. 2015). The assays were carried out using the antibodies W1 and Kfu 2 that were used in DE 197 58 017 C2. In said assays, W1 is the primary antibody directed against the P40 BDV nucleoprotein and Kfu 2 is the primary antibody directed against phosphorylated P protein P24 phosphoprotein of BDV. The assay set-up for the CIC detection and for the antibody detection follow the respective schemas in FIGS. 3 and 4.

Figure 1:
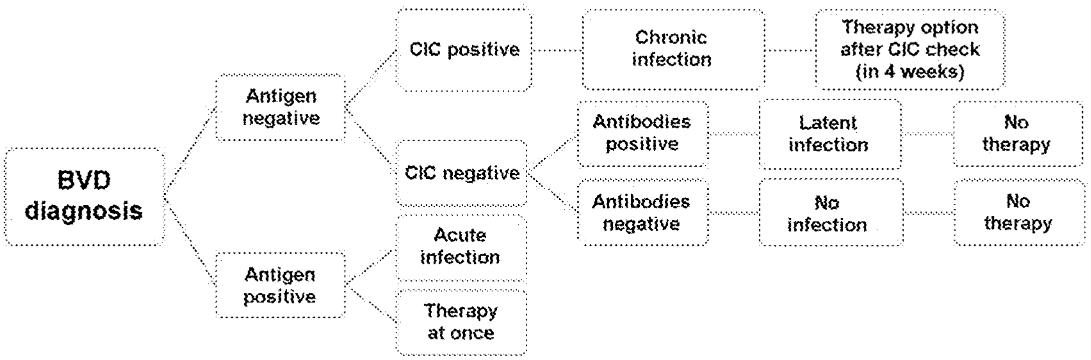
FIG. 1 shows the diagnosis schema for acute, chronic and latent BDV infections. In a first assay, what is assayed in accordance with the method according to the invention is the presence of the antigen. In the event of the presence thereof, there is an acute infection, whereas in the event of a negative detection, a further check is made to determine whether CIC are present or not. If CIC are present, a chronic infection is assumed, and in the case of CIC-negative samples, an additional check is made to determine whether antibodies are present. If no antibodies are present either, the existence of an infection is excluded, whereas in the case of the exclusive detection of antibodies (anti-p24 protein and/or anti-p40 protein antibodies), a latent infection is assumed.
Figure 2:
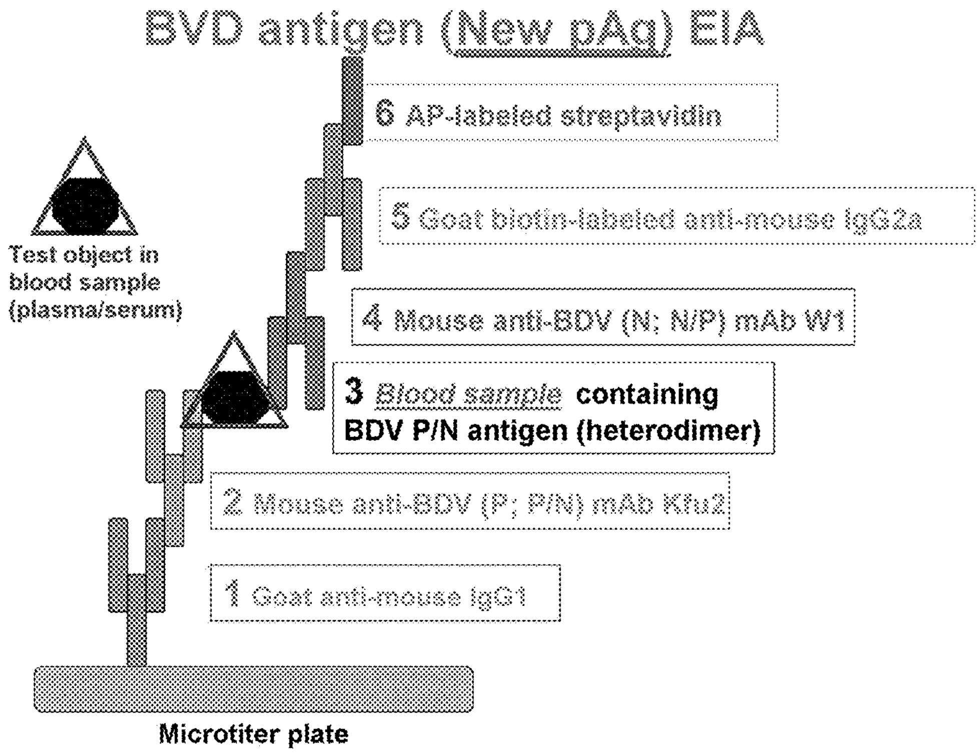
FIG. 2 shows a schema of the BDV antigen enzyme immunoassay (EIA) in accordance with the method according to the invention. In said assay, the monoclonal mouse antibody Kfu2 directed against phosphorylated p24 protein is immobilized on a microtiter plate via binding to a secondary antibody having anti-mouse IgG1 subclass specificity and then used for capture of the heterodimers from the plasma/serum sample. These bound heterodimers are then detected using the monoclonal mouse antibody W1 directed against p40 protein. To visualize the reaction, what follows is a secondary antibody having anti-mouse IgG2a subclass specificity, via the label of which with biotin reporter molecule and subsequent streptavidin-mediated binding of alkaline phosphatase, it is possible to effect the corresponding color reaction after addition of the substrate p-nitrophenyl phosphate.

The assay set-up of the method according to the invention for antigen detection (heterodimers) follows the schema in FIG. 2.

Material of Method According to the Invention:

AffiniPure goat anti-mouse IgG1, Fc fragment-specific antibodies (concentration 1.3 mg of antibody per ml), minimal cross-reaction with human, bovine and leporine serum proteins (code number 115-005-205, Jackson ImmunoResearch).

Biotin-SP-conjugated AffiniPure goat anti-mouse IgG2a, Fc fragment-specific antibodies, minimal cross-reaction with human, bovine and leporine serum proteins (code number 115-065-206, Jackson ImmunoResearch).

Alkaline phosphatase-conjugated streptavidin (code number 016-050-084, Jackson ImmunoResearch).

Alkaline phosphatase substrate kit (code number 172-1063, Biorad) or individual substances for substrate buffer and substrate (Bode et al., 2001) as follows:

Substrate buffer, diethanolamine buffer pH 9.8 (diethanolamine 1.007 M+$MgCl_2.6H_2O$ 0.5 mM+$NaN_3$ 0.003 M); Substrate, p-nitrophenyl phosphate hexahydrate (pNPP.6 $H_2O$) (0.003 M); 5 mg tablets (code number N9389 Sigma Aldrich); always prepare fresh in the assay, 1 mg of pNPP per ml of substrate buffer.

Conjugate buffer (alkaline phosphatase) TBS-Tween pH 8.0 (TRIS 0.02 M+NaCl 0.14 M+KCl 0.003 M+0.05% Tween 20).

Wash buffer, NaCl-Tween (0.9% NaCl+0.05% Tween 20+NaN3 0.003 M).

Sample dilution buffer (also for steps 2, 4 and 5 in FIG. 2), PBS-Tween pH 7.2 ($KH_2PO_4$ 0.0015 M+$Na_2HPO_4.12$ $H_2O$ 0.008 M+NaCl 0.14 M+KCl 0.003 M+0.05% Tween 20+$NaN_3$ 0.003 M).

Coating buffer, 0.01 M sodium phosphate/0.25 M NaCl pH 7.6 ($NaH_2PO_4.2$ $H_2O$ 0.02 M [stock A], $Na_2HPO_4$ 0.02 M [stock B]; coating buffer contains 65 ml of stock A+435 ml of stock B+0.25 M NaCl in 1000 ml of double-distilled water).

Stop solution, 3 M NaOH

All chemical substances with degree of purity as specified by American Chemical Society (ACS grade), preferably by Sigma Aldrich.

Nunc-Immuno 96-well microtiter plates for ELISA, MaxiSorp, F (flat bottom) (code number 442404, Nunc).

BDV-Specific Key Reagents

W1 (mouse subclass IgG2a) specifically directed against the nuclear BDV protein (N protein);

Kfu2 (mouse subclass IgG1) specifically directed against the BDV phosphoprotein (P protein);

W1 and Kfu2 are monoclonal mouse antibodies, first described by Ludwig et al., 1993.

The inventors have hybridoma supernatants of these two antibodies, which were already produced and which are suitable for assay kit production on an industrial scale. The inventors also have hybridoma cells which allow unlimited production of further batches of the monoclonal antibodies W1 and Kfu2.

Further characterization of W1 and Kfu2 (Bode, 2008)

| Short description | |
|---|---|
| | W1 |
| Species | Mouse |
| Subclone | TL9 |
| IgG subclass | IgG 2a |
| Specificity | N protein p40 of BDV (reference strain V) |
| Dissociation constant ($K_D$) | $2.31 \times 10^{-9}$ +− $0.26 \times 10^{-9}$M (native N protein) |
| Epitope type | Conformational epitope (discontinuous) |
| Hybridoma supernatant (=ready-to-use) | 1:500 usage dilution in BDV ELISAs |
| Recognition of recombinant (r) N protein | Yes (assay with earlier antigen ELISA) |
| Purified rN detection limit | 1.5-3 nanograms per mL |
| | Kfu2 |
| Species | Mouse |
| Subclone | 57-4-33 |
| IgG subclass | IgG 1 |
| Specificity | P protein p24 of BDV (reference strain V) |
| Dissociation constant ($K_D$) | $3.33 \times 10^{-9}$ +− $0.34 \times 10^{-9}$M (native P protein) |
| Epitope type | Conformational epitope (discontinuous) |
| Hybridoma supernatant (=ready-to-use) | 1:500 usage dilution in BDV ELISAs |
| Recognition of recombinant (r) P protein, nonphosphorylated | No (assay with earlier antigen ELISA) |
| Recognition of rP, phosphorylated in vitro | Yes (assay with earlier antigen ELISA) |

First Description of the Epitope Sequences of W1 and Kfu2

| Epitope on N protein p40 of BDV | SEQ ID No. | W1 |
|---|---|---|
| Epitope type | | Conformational epitope (discontinuous) |
| Number of binding sites | | Five on 5mer peptides (N1-N5) in each case |
| N1 | 3 | Amino acid sequence 32_KFLQY_36 |
| N2 | 4 | Amino acid sequence 116_AKFYG_120 |
| N3 | 5 | Amino acid sequence 168_TMMAA_172 |
| N4 | 6 | Amino acid sequence 294_LAPRS_298 |
| N5 | 7 | Amino acid sequence 307_FYWSK_311 |

Figure 7:
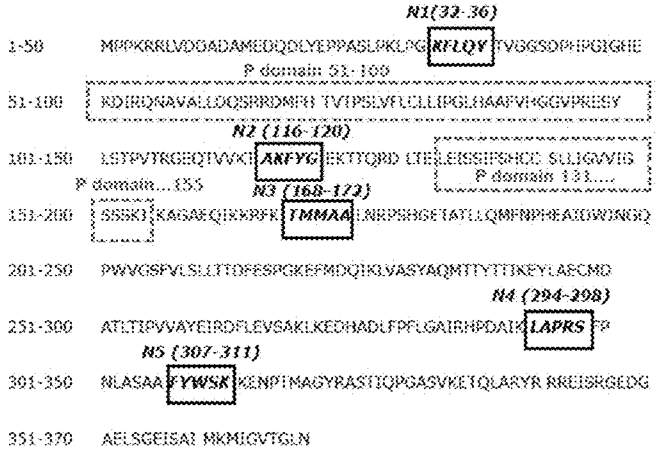
FIG. 7 shows the complete amino acid sequence of the BDV N protein (Seq. ID. No. 1). The five binding sites N1 to N5 (Seq. ID Nos. 3 to 7) for the described monoclonal antibody W1, identified by epitope mapping, form the conformational epitope on the native BDV N protein, wherein N1, N3 and N5 are interactive binding sites following crystal structure comparison (Bode, 2008). The binding sites are provided with a black frame. Provided with a dashed frame are the two domains which define the P protein binding sites on the N protein, amino acids 51-100 and 131-155 (Berg et al., 1998). These show no overlap with the W1 binding sites. As a result, N/P heterodimers can also be recognized.

See also FIG. 7

| Epitope on P protein p24 of BDV | SEQ ID No. | Kfu2 |
|---|---|---|
| Epitope type | | Conformational epitope (discontinuous) |
| Number of binding sites | | Three (15mer, 12mer, 5mer peptides), P1-P3 |
| P1, main domain, phosphorylation site serine 26/28 | 8 | Amino acid sequence 22_RRERSGSPRPRKVPR-36 |
| P2 | 9 | Amino acid sequence 46_LLKDLRKNPSMI_57 |
| P3 | 10 | Amino acid sequence 142_DRSMK_146 |

Figure 8:
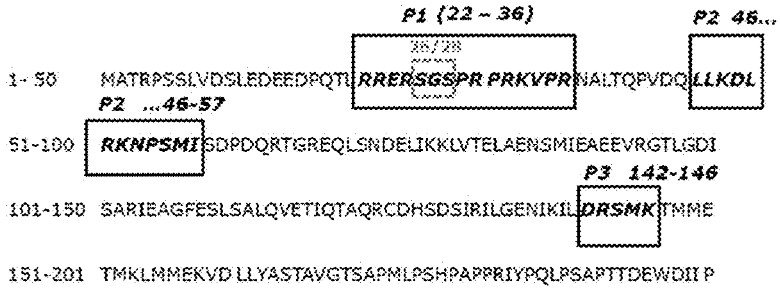
FIG. 8 shows the complete amino acid sequence of the BDV P protein (Seq. ID No. 2). The three binding sites P1 to P3 (Seq. ID. Nos. 8 to 10) for the described monoclonal antibody Kfu2, identified by epitope mapping, form the conformational epitope on the native P protein. The binding sites are provided with a black frame. P1 is the main binding site and includes the main phosphorylation site (S26/S28; Schwemmle et al., 1997) on the BDV P protein (provided with a dotted frame). Kfu2 recognizes only the active, phosphorylated BDV P protein (Bode, 2008).

See also FIG. 8

Protocol of Method According to the Invention:

100 µl each of a 1:1000 dilution of the goat anti-mouse IgG1 secondary antibody diluted with coating buffer are pipetted into the MaxiSorp F microtiter plates and incubated at 37° for one hour. Thereafter, three wash cycles are carried out with the wash buffer (120 ml total). Afterwards, the monoclonal antibody Kfu2 in a dilution of 1:500 (hybridoma supernatant) in PBS-Tween is incubated, at 100 µl per well, at 37° C. for one hour, followed by three wash cycles with the wash buffer. The samples (diluted 1:10 with PBS-Tween) are pipetted, at 100 µl each per well, into the microtiter plate and incubated at 37° C. for one hour, followed by three wash cycles with wash buffer. Thereafter, the monoclonal antibody W1 in a dilution of 1:500 as hybridoma supernatant diluted in PBS-Tween is added at 100 µl per well, incubated at 37° C. for one hour, followed by three wash cycles. Thereafter, the goat anti-mouse IgG2a secondary antibody labeled with biotin in a dilution of 1:1000 in PBS-Tween is added in an amount of 100 µl per well, incubated at 37° C. for one hour and subsequently washed with three wash cycles.

Then, the alkaline phosphatase-labeled streptavidin, diluted 1:1000 in conjugate buffer TBS-Tween pH 8.0, is added in an amount of 100 µl per well and incubated at 37° C. for 30 min. This is followed by again three wash cycles with wash buffer.

Thereafter, the detection reaction takes place with p-nitrophenyl phosphate (1 mg/ml) p-NPP in substrate buffer pH 9.8. 100 µl each of the corresponding p-NPP solution are added, followed by an incubation at room temperature for 2.5 minutes. Note: continuous visual monitoring is necessary, the negative control must remain colorless, whereas the positive control changes color. The color reaction is stopped by addition of the stop solution (3 M NaOH) at 50 µl each per well. The absorbance is immediately determined at 405 nm using a suitable multichannel photometer. "Blank" measurement against unconverted substrate.

CIC Determination as Per the Methods Described in DE 19758017 C2

Figure 3:
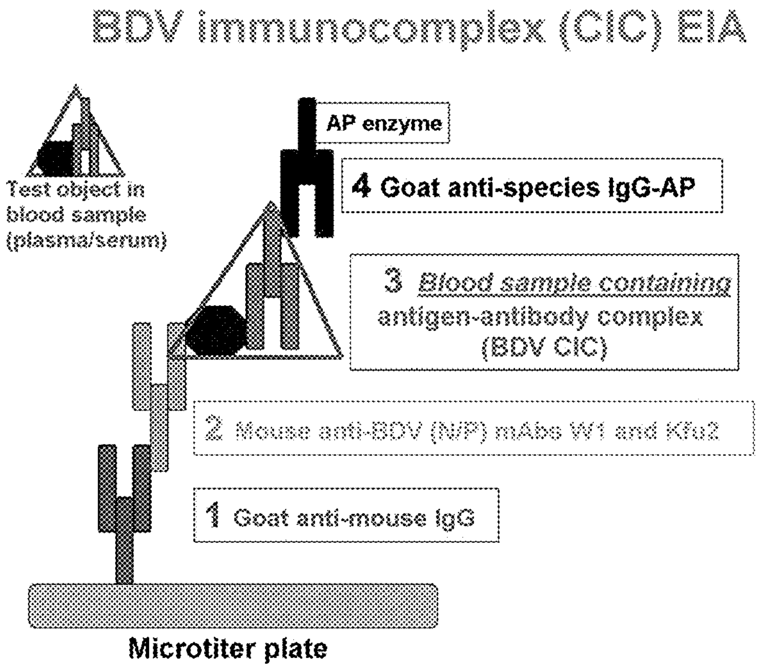
FIG. 3 shows a schema of the BDV immunocomplex EIA, as described in DE 19758017 C2 for example. There, the two monoclonal mouse antibodies W1 and Kfu2 are immobilized on a microtiter plate via binding to a secondary antibody having anti-mouse IgG specificity and then used for capture of the antigenantibody complexes from the plasma/serum sample. Said antigenantibody complexes (BDV CIC) are then detected using enzyme-labeled secondary antibodies directed against the IgG of the host species of the sample (alkaline phosphatase reporter molecule) and a corresponding color reaction (as in FIG. 2).

CIC determination in the samples was carried out as per the methods described in DE 19758017 C2 (see above schema in FIG. 3). To optimize the diagnostic assay for CIC determination in practice, the incubation times and temperatures were simplified to respectively 1 h at 37° C. for all steps, except for the visualization steps, i.e., the substrate incubation (C3), stop-solution addition (C4) and measurement (C5). With regard to the monitoring of the development of the color reaction, the procedure was as above for the invention described here. The initial dilution of the samples to be assayed of 1:20 in single determination with validation on positive and negative control offers the same reliability as the inclusion of further dilutions.

In the description of the materials, the code numbers are added below: AffiniPure goat anti-mouse IgG, Fc fragment-specific antibodies (code No. 115-005-071; Jackson ImmunoResearch).

Alkaline phosphatase-conjugated AffiniPure goat anti-human IgG, Fc fragment-specific antibodies, minimal cross-reaction with bovine, equine and murine serum proteins (code No. 109-055-098; Jackson ImmunoResearch) for human samples.

Alkaline phosphatase-conjugated AffiniPure goat anti-horse IgG, Fc fragment-specific antibodies (code No. 108-055-008; Jackson ImmunoResearch) for horse samples. Key reagents W1 and Kfu2, substrate kit or substrate buffer and substrate tablets, buffer and Nunc MaxiSorp F ELISA plates as described above for the new invention.

Antibody Determination in Plasma/Serum as Per the Methods Described in DE 19758017 C2

Figure 4:
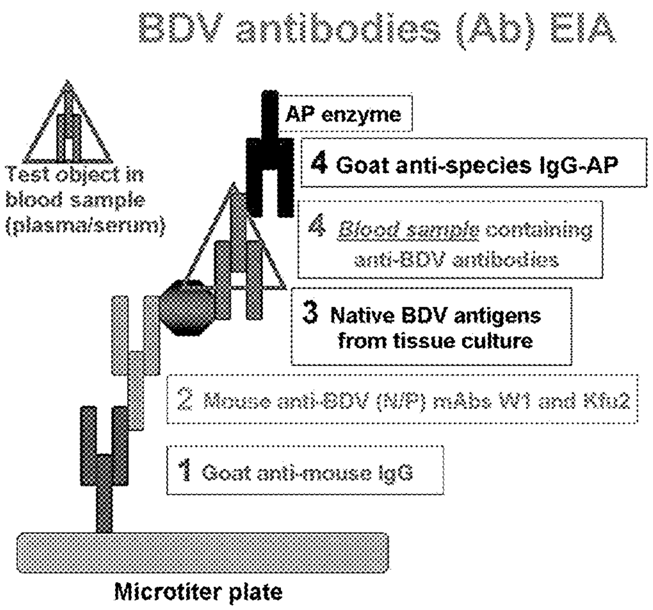
FIG. 4 shows a schema of the BDV antibody EIA, as can be used according to the invention. Here, the monoclonal antibodies W1 and Kfu2 that were described are likewise immobilized on a microtiter plate via binding to a secondary antibody having anti-mouse IgG specificity and then used as capture antibodies for first binding native BDV antigens, which had been previously obtained in virus-free form from a standardized infected cell culture. These bound BDV antigens then make it possible to detect anti-BDV antibodies (anti-p24 or anti-p40 protein antibodies) from a plasma/serum sample. This is, after binding of anti-BDV antibodies present in the sample to the native antigen, then effected via enzyme-labeled secondary antibodies directed against the IgG of the host species of the sample (alkaline phosphatase reporter molecule) and a corresponding color reaction (as in FIG. 2).

The determination of the antibodies against the p24 protein and/or p40 protein in plasma/serum samples was in principle carried out as per the method described in DE 19758017 C2 (see above scheme in FIG. 4). Analogously to the CIC assay, the incubation times and temperatures were simplified to respectively 1 h at 37° C. for all steps, except for the visualization steps, to optimize the diagnostic kit for the antibody determination in practice. Furthermore, instead of the described initial dilution of the samples of 1:50, the dilution was adjusted to 1:100. It became apparent that the initial dilution of the samples to be assayed for antibodies of 1:100 in single determination with validation on positive and negative control offers the same reliability as the inclusion of further dilutions.

To carry out the BDV antibody EIA described in DE 19758017 C2, detection antigen from BDV-infected cells is required. The usage dilution of the detection antigens from infected cell cultures is, depending on the batch, between 1:100 and 1:300.

A human oligodendroglial cell line (OLIGO/TL) persistently infected with BDV strain V (Briese et al., 1994) that allows the unlimited production of detection antigen was deposited at the German Collection of Microorganisms and Cell Cultures (DSMZ) in Braunschweig on 12 Dec. 1997 under No. DSM ACC2334.

For the description of the remaining materials, see the CIC assay.

Figure 5:
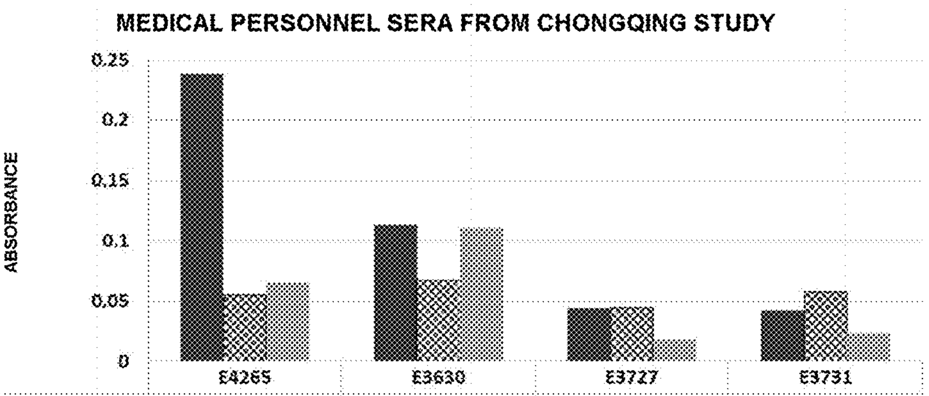
FIG. 5 shows the results of antigen assays for individual samples from test persons, wherein, firstly, BDV antigen is detected using the method according to the invention (New pAg) and, secondly, using the earlier antigen detection method described from DE 198 60 255 C2 (Old pAg).

Results:

FIG. 5 shows a comparison of the method according to the invention with the prior antigen assay. Since the prior antigen assay works with a sample dilution of 1:2, the results thereof are included both for this dilution and for the dilution of 1:10 applicable to the assay according to the invention.

FIG. 5 shows that sample E4265 was positive only with the assay according to the invention, whereas it was not recognized with the prior antigen assay, neither at 1:10 nor at 1:2 sample dilution. Sample E3630 was weakly positive with the assay according to the invention. The positive signal was confirmed in a further analysis (table and FIG. 6). The prior antigen assay likewise showed a weakly positive to borderline positive signal, though only at the 1:2 dilution. The next dilution step 1:4 was already distinctly negative with absorbance value 0.034 (not depicted), and this led to a negative assessment. Because of the high sample volume for a dilution series from 1:2, i.e., 100 μl, a repetition was no longer possible.

Samples E3727 and E3731 were negative in both antigen assays, even at the dilution of 1:2 in the case of the prior antigen assay. Both samples originate from the physician/nurse team in the eye care department of the hospital. However, the combination with the CIC assay shows that both were chronically infected with BDV (see the table). Team member E3731 had high CIC values and additionally antibodies, indicating an acute bout of virus that had recently taken place.

In the case of samples E4265 and E3630, who were positive only with the new assay at 1:10 sample dilution, it should be emphasized that the prior assay, even at its sample dilution of 1:2 that is five times lower as standard, was not capable or not unambiguously capable of detecting BDV antigens. The assay according to the invention thus had at least a five-times higher sensitivity than the prior assay and was able to demonstrate that the medical coworkers (E4265 female, research; E3630 female, retired) went through an acute BDV infection at the sampling time point. If only the prior antigen assay had been available, the diagnosis "chronic infection" would have had to been made on the basis of the simultaneous detection of CIC, and the acute exposure would have been overlooked (see the table).

Figure 6:
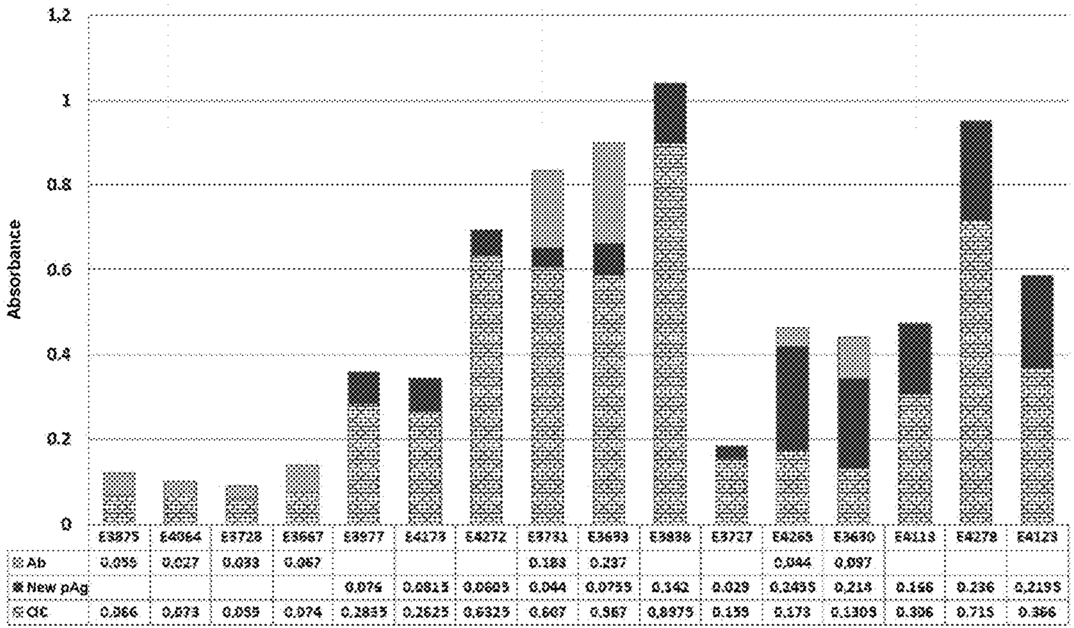
FIG. 6 shows the results of the combined use of the antigen assay according to the invention with the CIC assay and the antibody assay, the last two assays as described in DE 19758017 C2. The absorbance values are shown cumulatively.

Results of the combined use of the antigen assay according to the invention with the CIC assay and the antibody (Ab) assay as per DE 19758017 C2 are shown by FIG. 6. The values from Table 1 are thus clearly depicted by cumulative columns.

FIG. 6 illustrates that the assay according to the invention was able to identify six acute infections in the example panel (E4123, E 4278, E4113, E3630, E 4265 and E3838). Negative results in the assay according to the invention were, in combination with the CIC assay, able to identify six chronic infections (E3727, E3693, E3731, E4272, E4173, E3977). Negative CIC and antibody assays were, in four cases from the panel, able to exclude a BDV infection (E3667, E3728, E4064, E3875).

The sample panel of medical personnel for which there was no mental disorders according to a structured interview, neither earlier nor currently, was chosen in order to show that the assay according to the invention, alone and in combination with CIC assay and antibody assay, is, independently of clinical symptoms, capable of differentiating between acute, chronic and latent infections and of excluding a BDV infection with analysis of a single blood sample. Chronic stress is common in everyday life in the medical sector, and so an increased activation risk does not appear unusual. In addition, there is an increased infection risk in the daily care of sick people.

The volume of 100 μl for the prior antigen assay, with initial 1:2 dilution and subsequent dilution series, which volume is distinctly higher in comparison with the antigen assay according to the invention, was only available for selective parallel tests, as shown in FIG. 5, for the study samples already analyzed multiple times elsewhere.

The advantages of the new method according to the invention for antigen detection are also multifarious and practical without direct comparison.

Firstly, what is possible is a broad applicability for a very wide variety of different sample materials, i.e., for any type of body fluid or tissue fluid. BDV activity is measured independently of the host species. Furthermore, the determination of the phosphorylated heterodimers composed of p24 and p40 allows the verification of acute BDV infections, since the primary antibody Kfu2 only binds the active phosphorylated form of the BDV P protein. For the monoclonal antibody Kfu2 used here, this is globally a unique feature.

In contrast to the assay described in DE 19758017 C2, what is presently determined is the heterodimer. In contrast, the prior method is based on two capture antibodies, i.e., immobilized primary antibodies against both p24 and p40, being used in order to also determine monomeric forms thereof. Accordingly, however, it was not possible to differentiate the present phosphorylated heterodimers therewith. In one embodiment, the method according to the invention uses, in addition, secondary antibodies which allow a high level of reproducibility. In the embodiment with the binding pair biotinstreptavidin coupled to an enzyme such as alkaline phosphatase, a signal enhancement and thus improved detectability is achieved compared to the prior visualization of the signal solely via enzyme-labeled anti-antibodies. Furthermore, significantly less patient sample (10 μl for one-time determination, 20 μl for dilution series from 1:10)

is required, and the sensitivity of the method is higher according to the five-times higher initial dilution of the sample of 1:10. This became especially apparent by it being possible to identify an acute BDV infection in more individuals than with the prior antigen assay.

The present invention provides a completely new assay method for acute BDV infections that has a higher sensitivity than the prior antigen assay and is independent of limited resources, as represented by rabbit antibodies for example. By combination with CIC assay and antibody assay, the new method is capable of reliably distinguishing between acute, chronic and latent infections (humans and animals) and of thereby raising BDV diagnostics to a hitherto unreached level of informative value with a high standard of quality.

The method according to the invention is therefore suitable especially for diagnosis, but also for course monitoring of a BDV infection, especially also for determination of the therapy plan. Furthermore, the method according to the invention can be part of a treatment method.

The previously unpublished amino acid sequences of the binding sites which form the respective conformational epitopes are named for the first time here. They are essential molecular constituents of the properties of the monoclonal antibodies W1 and Kfu2.

The present invention provides a completely new assay method for acute BDV infections that is independent of limited resources and can be used in humans and animals in an overarching manner as regards species. By combination of the new diagnostic kit with the use of known methods or kits for detecting circulating immunocomplexes (CIC) and antibodies in the plasma or serum, the new method is capable of reliably distinguishing between acute, chronic and latent infections (humans and animals) and of reaching a hitherto unreached level of informative value in BDV diagnostics.

CITED LITERATURE (IN ALPHABETICAL ORDER)

Berg M, et al., J Gen Virol. 1998; 79 (Pt 12):2957-2963.
Bode L. Human Bornavirus infection towards a valid diagnostic system. APMIS Suppl 124, 2008; 116: 21-39.
Bode L, et al. The Lancet 1997; 349: 178-179.
Bode L, et al. Mol Psychiatry 1996; 1: 200-212.
Bode L, Ludwig H. Borna disease virus infection, a human mental-health risk. Clin Microbiol Rev. 2003; 16(3):534-545. Review.
Bode L, et al. Mol Psychiatry 2001; 6: 481-491.
Briese T, et al. Proc Natl Acad Sci USA. 1994; 91(10):4362-4366.
Cubitt B, et al. J Virol. 1994; 68(3):1382-1396.
Dietrich D E, Bode L. Human Borna disease virus infection and its therapy in affective disorders. APMIS Suppl 124, 2008; 116: 61-65.
Dietrich D E, et al. Bipolar Disorder 2000; 2: 65-70.
Ferszt R, et al. Pharmacopsychiatry 1999; 32 (4):142-147
Liu X, et al. Virol J. 2015; 12: 39.
Ludwig H, et al. Arch Virol 1993; Suppl 7:111-133.
Rudolph M, et al. Structure 2003; 11: 1219-1226.
Schwemmle M, et al. J Biol Chem. 1997; 272(35):21818-21823

The invention claimed is:

1. A method for detecting acute Borna disease virus (BDV) infections, comprising: the step of determining a presence of heterodimers composed of phosphorylated p24 BDV phosphoprotein and p40 BDV nucleoprotein in a sample using a sandwich enzyme-linked immunosorbent assay (ELISA), wherein a first primary antibody is present in an immobilized state and is incubated with the sample, wherein a second primary antibody is added in a non-immobilized state after incubation of the sample with the first antibody, wherein either the first primary antibody is directed against a phosphorylated p24 BDV phosphoprotein and the second primary antibody is directed against a p40 BDV nucleoprotein and/or wherein the first primary antibody and the second primary antibody are monoclonal antibodies.

2. The method as claimed in claim 1 wherein the immobilized first primary antibody is present in an immobilized state on a surface via a first secondary antibody or is directly immobilized on the surface.

3. The method as claimed in claim 1, wherein the non-immobilized primary second antibody is identified using a second secondary antibody comprising a reporter molecule.

4. The method as claimed in claim 1 wherein the first primary antibody and the second primary antibody originate from different species.

5. The method as claimed in claim 1 wherein the first primary antibody is present in an immobilized state directly on a surface or via a first secondary antibody on the surface, wherein the non-immobilized primary second antibody is identified using a second secondary antibody comprising a reporter molecule, wherein the first and second secondary antibodies are from different species or originate from the same species.

6. The method as claimed in claim 1 further comprising detecting circulating immunocomplexes (CIC) composed of BDV antigens and specific antibodies attached thereto.

7. The method as claimed in claim 1 further comprising detecting circulating free antibodies against p24 protein and/or the p40 protein.

8. A diagnostic kit for a sandwich ELISA for detecting acute BDV infections, comprising:

a first primary antibody and a second primary antibody, a first of said first and second primary antibodies being directed against the phosphorylated p24 BDV phosphoprotein and a second of said first and second primary antibodies being directed against the p40 BDV nucleoprotein;

at least one secondary antibody labeled with a reporter molecule;

optionally means for immobilizing a primary antibody on a surface; and instructions for carrying out a method as claimed in claim 1.

9. The diagnostic kit for a sandwich ELISA for detecting acute BDV infections as claimed in claim 8 wherein the first primary antibody is present in an immobilized state directly on a surface or via a first secondary antibody on the surface, wherein the nonimmobilized primary second antibody is identified using a second secondary antibody comprising a reporter molecule, wherein the first and second secondary antibodies are from different species or originate from the same species.

10. The diagnostic kit as claimed in claim 8, further comprising means for detecting CIC composed of BDV antigens and specific antibodies attached thereto.

11. The diagnostic kit as claimed in claim 8, further comprising means for detecting circulating free antibodies against the p24 protein and/or p40 protein in the plasma/serum.

12. The method as claimed in claim 1 wherein p40 BDV nucleoprotein epitopes recognized by said second primary antibody do not overlap with a BDV phosphoprotein binding domain on the BDV nucleoprotein.

13. The method of claim 6 wherein the CIC BDV antigens include all or a portion of p24 protein and/or p40 protein.

14. A method for determining a prevalence of BDV infection differentiating acute, chronic, and latent states in an epidemiological study of a population's mental and/or physical health comprising performing the method of claim 1 on a plurality of different samples drawn from the population;

detecting circulating immunocomplexes (CIC) composed of BDV antigens and specific antibodies attached thereto in the samples; and detecting circulating free antibodies against p24 protein and/or the p40 protein in the samples, wherein presence of the heterodimers is indicative of an acute BDV infection, wherein absence of the heterodimers and presence of the CIC is indicative of a chronic BDV infection, and wherein absence of the heterodimers and the CIC and presence of the circulating free antibodies is indicative of a latent BDV infection.

15. A method for diagnosing BDV infection differentiating acute, chronic, and latent states in a patient with a psychiatric and/or neurological disorder comprising performing the method of claim 1 on a sample taken from the patient;

detecting circulating immunocomplexes (CIC) composed of BDV antigens and specific antibodies attached thereto in the sample; and detecting circulating free antibodies against p24 protein and/or the p40 protein in the sample, wherein presence of the heterodimers is indicative of an acute BDV infection, wherein absence of the heterodimers and presence of the CIC is indicative of a chronic BDV infection, and wherein absence of the heterodimers and the CIC and presence of the circulating free antibodies is indicative of a latent BDV infection.

16. A method for monitoring the course of a BDV infection in a patient comprising periodically differentiating acute, chronic, and latent states by performing the method of claim 1 on samples obtained from the patient at different time periods;

detecting circulating immunocomplexes (CIC) composed of BDV antigens and specific antibodies attached thereto in the samples; and detecting circulating free antibodies against p24 protein and/or the p40 protein in the samples, wherein presence of the heterodimers is indicative of an acute BDV infection, wherein absence of the heterodimers and presence of the CIC is indicative of a chronic BDV infection, and wherein absence of the heterodimers and the CIC and presence of the circulating free antibodies is indicative of a latent BDV infection.

17. A method for differential diagnosis of acute BDV infections from chronic and latent infections comprising performing the method of claim 1 on a sample of a patient and comparing results obtained to standards for chronic and latent infections, wherein the standards are obtained by detecting circulating immunocomplexes (CIC) composed of BDV antigens and specific antibodies attached thereto in the sample; and detecting circulating free antibodies against p24 protein and/or the p40 protein in the sample wherein presence of the heterodimers is indicative of an acute BDV infection, wherein absence of the heterodimers and presence of the CIC is indicative of a chronic BDV infection, and wherein absence of the heterodimers and the CIC and presence of the circulating free antibodies is indicative of a latent BDV infection.

* * * * *

SEQUENCE LISTING

```
<160> NUMBER OF SEQ ID NOS: 10

<210> SEQ ID NO 1
<211> LENGTH: 370
<212> TYPE: PRT
<213> ORGANISM: Borna Disease Virus

<400> SEQUENCE: 1

Met Pro Pro Lys Arg Arg Leu Val Asp Asp Ala Asp Ala Met Glu Asp
1               5                   10                  15

Gln Asp Leu Tyr Glu Pro Pro Ala Ser Leu Pro Lys Leu Pro Gly Lys
            20                  25                  30

Phe Leu Gln Tyr Thr Val Gly Gly Ser Asp Pro His Pro Gly Ile Gly
        35                  40                  45

His Glu Lys Asp Ile Arg Gln Asn Ala Val Ala Leu Leu Asp Gln Ser
    50                  55                  60

Arg Arg Asp Met Phe His Thr Val Thr Pro Ser Leu Val Phe Leu Cys
65                  70                  75                  80

Leu Leu Ile Pro Gly Leu His Ala Ala Phe Val His Gly Gly Val Pro
                85                  90                  95

Arg Glu Ser Tyr Leu Ser Thr Pro Val Thr Arg Gly Glu Gln Thr Val
            100                 105                 110

Val Lys Thr Ala Lys Phe Tyr Gly Glu Lys Thr Thr Gln Arg Asp Leu
        115                 120                 125

Thr Glu Leu Glu Ile Ser Ser Ile Phe Ser His Cys Cys Ser Leu Leu
    130                 135                 140

Ile Gly Val Val Ile Gly Ser Ser Ser Lys Ile Lys Ala Gly Ala Glu
145                 150                 155                 160
```

-continued

```
Gln Ile Lys Lys Arg Phe Lys Thr Met Met Ala Ala Leu Asn Arg Pro
                165                 170                 175

Ser His Gly Glu Thr Ala Thr Leu Leu Gln Met Phe Asn Pro His Glu
            180                 185                 190

Ala Ile Asp Trp Ile Asn Gly Gln Pro Trp Val Gly Ser Phe Val Leu
        195                 200                 205

Ser Leu Leu Thr Thr Asp Phe Glu Ser Pro Gly Lys Glu Phe Met Asp
    210                 215                 220

Gln Ile Lys Leu Val Ala Ser Tyr Ala Gln Met Thr Thr Tyr Thr Thr
225                 230                 235                 240

Ile Lys Glu Tyr Leu Ala Glu Cys Met Asp Ala Thr Leu Thr Ile Pro
                245                 250                 255

Val Val Ala Tyr Glu Ile Arg Asp Phe Leu Glu Val Ser Ala Lys Leu
            260                 265                 270

Lys Glu Asp His Ala Asp Leu Phe Pro Phe Leu Gly Ala Ile Arg His
        275                 280                 285

Pro Asp Ala Ile Lys Leu Ala Pro Arg Ser Phe Pro Asn Leu Ala Ser
    290                 295                 300

Ala Ala Phe Tyr Trp Ser Lys Lys Glu Asn Pro Thr Met Ala Gly Tyr
305                 310                 315                 320

Arg Ala Ser Thr Ile Gln Pro Gly Ala Ser Val Lys Glu Thr Gln Leu
                325                 330                 335

Ala Arg Tyr Arg Arg Arg Glu Ile Ser Arg Gly Glu Asp Gly Ala Glu
            340                 345                 350

Leu Ser Gly Glu Ile Ser Ala Ile Met Arg Met Ile Gly Val Thr Gly
        355                 360                 365

Leu Asn
    370
```

<210> SEQ ID NO 2
<211> LENGTH: 201
<212> TYPE: PRT
<213> ORGANISM: Borna Disease Virus

<400> SEQUENCE: 2

```
Met Ala Thr Arg Pro Ser Ser Leu Val Asp Ser Leu Glu Asp Glu Glu
1               5                   10                  15

Asp Pro Gln Thr Leu Arg Arg Glu Arg Ser Gly Ser Pro Arg Pro Arg
            20                  25                  30

Lys Val Pro Arg Asn Ala Leu Thr Gln Pro Val Asp Gln Leu Leu Lys
        35                  40                  45

Asp Leu Arg Lys Asn Pro Ser Met Ile Ser Asp Pro Asp Gln Arg Thr
    50                  55                  60

Gly Arg Glu Gln Leu Ser Asn Asp Glu Leu Ile Lys Lys Leu Val Thr
65                  70                  75                  80

Glu Leu Ala Glu Asn Ser Met Ile Glu Ala Glu Glu Val Arg Gly Thr
                85                  90                  95

Leu Gly Asp Ile Ser Ala Arg Ile Glu Ala Gly Phe Glu Ser Leu Ser
            100                 105                 110

Ala Leu Gln Val Glu Thr Ile Gln Thr Ala Gln Arg Cys Asp His Ser
        115                 120                 125

Asp Ser Ile Arg Ile Leu Gly Glu Asn Ile Lys Ile Leu Asp Arg Ser
    130                 135                 140

Met Lys Thr Met Met Glu Thr Met Lys Leu Met Met Glu Lys Val Asp
145                 150                 155                 160
```

Leu Leu Tyr Ala Ser Thr Ala Val Gly Thr Ser Ala Pro Met Leu Pro
165 170 175

Ser His Pro Ala Pro Pro Arg Ile Tyr Pro Gln Leu Pro Ser Ala Pro
180 185 190

Thr Thr Asp Glu Trp Asp Ile Ile Pro
195 200

<210> SEQ ID NO 3
<211> LENGTH: 5
<212> TYPE: PRT
<213> ORGANISM: Borna disease Virus

<400> SEQUENCE: 3

Lys Phe Leu Gln Tyr
1 5

<210> SEQ ID NO 4
<211> LENGTH: 5
<212> TYPE: PRT
<213> ORGANISM: borna virus disease

<400> SEQUENCE: 4

Ala Lys Phe Tyr Gly
1 5

<210> SEQ ID NO 5
<211> LENGTH: 5
<212> TYPE: PRT
<213> ORGANISM: Borna Disease Virus

<400> SEQUENCE: 5

Thr Met Met Ala Ala
1 5

<210> SEQ ID NO 6
<211> LENGTH: 5
<212> TYPE: PRT
<213> ORGANISM: Borna Disease Virus

<400> SEQUENCE: 6

Leu Ala Pro Arg Ser
1 5

<210> SEQ ID NO 7
<211> LENGTH: 5
<212> TYPE: PRT
<213> ORGANISM: Borna Disease Virus

<400> SEQUENCE: 7

Phe Tyr Trp Ser Lys
1 5

<210> SEQ ID NO 8
<211> LENGTH: 15
<212> TYPE: PRT
<213> ORGANISM: Borna Disease Virus

<400> SEQUENCE: 8

Arg Arg Glu Arg Ser Gly Ser Pro Arg Pro Arg Lys Val Pro Arg
1 5 10 15

<210> SEQ ID NO 9
<211> LENGTH: 12

-continued

```
<212> TYPE: PRT
<213> ORGANISM: Borna Disease Virus

<400> SEQUENCE: 9

Leu Leu Lys Asp Leu Arg Lys Asn Pro Ser Met Ile
1               5                   10


<210> SEQ ID NO 10
<211> LENGTH: 5
<212> TYPE: PRT
<213> ORGANISM: Borna Disease Virus

<400> SEQUENCE: 10

Asp Arg Ser Met Lys
1               5
```